United States Patent [19]

Malpass et al.

[11] 4,133,824
[45] Jan. 9, 1979

[54] ORGANO-MAGNESIUM COMPLEXES AND PROCESS FOR THEIR PREPARATION

[75] Inventors: Dennis B. Malpass, LaPorte; Joseph H. Merkley, Dayton, both of Tex.

[73] Assignee: Texas Alkyls, Inc., Deer Park, Tex.

[21] Appl. No.: 825,370

[22] Filed: Aug. 17, 1977

[51] Int. Cl.$^2$ .................. B01J 31/02; B01J 31/12; C07F 3/02
[52] U.S. Cl. .................. 260/448 AD; 252/431 R; 252/431 C; 252/429 C; 260/665 G; 260/429 R
[58] Field of Search .......... 252/431 R, 431 C, 429 C; 260/665 G, 448 AD, 448 R, 429 R

[56] References Cited

U.S. PATENT DOCUMENTS

| | | | |
|---|---|---|---|
| 3,737,393 | 6/1973 | de Vries | 252/431 R |
| 3,989,878 | 11/1976 | Aishima et al. | 252/429 C X |
| 4,004,071 | 1/1977 | Aishima et al. | 252/429 C X |
| 4,027,089 | 5/1977 | Aishima et al. | 252/429 C X |

OTHER PUBLICATIONS

Malpass et al., J. Organometallic Chem., 93 (1975), pp. 1-8.

*Primary Examiner*—Patrick Garvin
*Attorney, Agent, or Firm*—Edwin H. Baker

[57] ABSTRACT

Hydrocarbon soluble organo-magnesium complex of the formula $$(R_2'Mg)_m \cdot [(RO)_aM]_n$$

wherein R is a hydrocarbyl group or

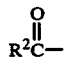

wherein $R^2$ is a hydrocarbyl group. R' is a primary alkyl group having 1 to 25 carbon atoms, or phenyl group, or mixture thereof, M is a group IIA or group IIIA metal and a is 2 or 3, and m and n are numbers such that the ratio of m/n is about one or greater.

These complexes are prepared by reacting magnesium metal with a primary alkyl halide or phenyl halide in the presence of a hydrocarbon solvent and adding thereto an oxygen containing metal compound of the formula $(RO)_aM$ wherein R, M and a are as defined. The oxygen containing metal compound functions as a solubilizing agent for organo-magnesium compounds which are normally only slightly soluble in hydrocarbon media. These complexes are characterized by very low halide content, lack of ether contamination, magnesium to M ratios of between about 1:2 to about 20:1 and hydrocarbon solubility.

26 Claims, No Drawings

ORGANO-MAGNESIUM COMPLEXES AND PROCESS FOR THEIR PREPARATION

BACKGROUND OF THE INVENTION

Dialkylmagnesium compounds are well known in the art. However, the production of soluble dialkylmagnesium compounds, free of solvation and chloride, by the direct reaction of magnesium with a halide, has heretofore been accomplished only recently.

U.S. Pat. No. 3,737,393 teaches hydrocarbon soluble alkyl magnesium-alkyl aluminum complexes prepared by interaction of certain organo-aluminum compounds with the reaction product of magnesium and certain alkyl halides. However, this patent does not teach or suggest the use of the oxygen containing metal compounds of this invention for interaction with the reaction product of the magnesium and the certain alkyl halides.

It is an object of the present invention to prepare hydrocarbon soluble organo-magnesium complexes, including those complexes containing the normally insoluble lower dialkylmagnesium compounds suitable for use as co-catalysts for the polymerization of olefins, diolefines, or olefin oxides.

It is another object of the present invention to prepare organo-magnesium complexes wherein the Mg/M ratio is about one or greater. Other objects of the present invention will become apparent from the description contained below.

DETAILED DESCRIPTION OF THE INVENTION

The present invention relates to a hydrocarbon soluble organo-magnesium complex of the formula $$(R_2'Mg)_m \cdot [(RO)_a M]_n$$

wherein R is a hydrocarbyl group, for example, an alkyl, cycloalkyl, aralkyl, aryl or alkaryl group; either substituted or unsubstituted, preferably R is a primary, secondary, or tertiary alkyl group having from 1 to 25 carbon atoms, preferably having 1 to 8 carbon atoms, most preferably having 2 to 4 carbon atoms or the group $$R^2\overset{O}{\underset{\|}{C}}-$$

wherein $R^2$ is a hydrocarbyl group, for example, an alkyl, cycloalkyl, aralkyl, aryl or alkaryl group; either substituted or unsubstituted; more preferably $R^2$ is alkyl having 1 to 20 carbon atoms or phenyl; even more preferably $R^2$ is alkyl having 2 to 4 carbon atoms or phenyl; most preferably phenyl and M is a group IIA or IIIA metal, preferably magnesium or aluminum and a is the integer 2 when M is a group IIA metal and 3 when M is a group IIIA metal. R' is a primary alkyl group having 1 to 25 carbon atoms, preferably 1 to 10 carbon atoms or phenyl group, or mixture thereof, more preferably a primary alkyl having 1 to 4 carbon atoms, and m and n are numbers such that the ratio of m/n is about one or greater, preferably between about 1 to 10. As an illustration, R can be methyl, ethyl, n-propyl, isopropyl, n-butyl, isobutyl, sec.-butyl or t-butyl. R' can be methyl, ethyl, n-propyl, n-butyl, or n-amyl and to a process for its preparation.

These organo-magnesium complexes are prepared by (1) reacting magnesium metal with a primary alkyl halide or phenyl halide in the presence of a hydrocarbon solvent and (2) adding thereto an oxygen containing metal compound of the formula $(RO)_a M$ wherein R, M and a are as defined, preferably after the completion of the reaction.

Illustrative of these organo-magnesium compounds are the following: dimethylmagnesium, diethylmagnesium, di-n-propylmagnesium, di-n-butylmagnesium, di-n-amylmagnesium, di-n-hexylmagnesium, diphenylmagnesium, and the like. The preferred compounds are dimethylmagnesium, diethylmagnesium, di-n-butylmagnesium and di-n-amylmagnesium. Particularly preferred are the primary alkyl magnesium compounds wherein the alkyl group is n-butyl and n-amyl.

The organo-magnesium moiety in the complexes of the present invention is generally derived from bis primary dialkyl- or diphenylmagnesium compounds, obtained via the direct reaction of magnesium with a primary alkyl or phenyl halide in a hydrocarbon solvent. Preferably the alkyl halide is not methyl chloride or ethyl chloride.

Although magnesium turnings or shavings of commercial grade that have been further activated by milling or any other of the known methods for activating magnesium can be used in the processes herein described for the preparation of organo-magnesium complexes, it is preferable to use magnesium in a finely divided state, for instance, as a powder with a particle size less than 100μ. With such fine particle size, it is unnecessary to activate the metal.

Although the Applicants do not wish to be held to a particular theory of the reaction mechanism, it is thought that the first reaction proceeds through a Grignard type intermediate $(R'MgX)_m$ which, in the absence of a solvating species, disproportionates via the Schlenk equilibrium to the organo-magnesium and magnesium halide as follows $$2mR'X + 2mMg \underset{2m}{\overset{}{\rightleftarrows}} (R'MgX) \longrightarrow mR_2'Mg + mMgX_2$$

wherein R' is as defined, X is chlorine, bromine or iodine, preferably chlorine, and m is an integer.

The extent of the disproportionation is dependent upon the nature of the solvent, the nature of the alkyl group and the particular halide involved.

As stated previously, the complexes of the present invention are prepared by initially reacting magnesium metal with a halide of the formula R'X wherein R' is as defined above and X is chlorine, bromine or iodine, preferably chlorine, and subsequently adding the oxygen containing metal compound directly to the reaction product, either during or after the reaction.

The magnesium and the halide are normally reacted in a molar ratio of 1.2 to 1.0, i.e., a 20% molar excess of magnesium. It is understood, however, that the ratio of reactants can be varied in the range from about 1 to 2 moles of magnesium per mole of halide, and preferably in the range from about 1.1 to 1.3, i.e., a 10–30% excess magnesium. This excess magnesium is desirable to minimize Wurtz coupling reactions.

Although the reaction of the halide with magnesium can be conducted in the absence of a solvent wherein an excess of the alkyl or phenyl halide serves as the dispersion medium, it is preferable that the reaction of the magnesium with the halide be conducted in a hydrocarbon solvent.

The term hydrocarbon solvent, as used herein, is used to designate any inert aliphatic and aromatic hydrocarbon. Illustrative of the hydrocarbons which can be used in the present invention are the following: isopentane, n-hexane, n-heptane, n-octane, cyclohexane, methylcyclohexane, benzene, and toluene and halogenated aromatic hydrocarbons such as chlorobenzene. Particularly preferred solvents are those aliphatic and aromatic hydrocarbons which boil between 69° and 100° C. Particularly preferred aliphatic and cycloaliphatic hydrocarbons are those having 5 to 20 carbon atoms especially alkyl, cycloalkyl, aryl and alkaryl hydrocarbons having from 6 to 15 carbon atoms. The most preferred solvents are n-heptane, cyclohexane and benzene. The hydrocarbon solvent is normally employed in amounts from about 10 to 20 times the weight of magnesium charged.

The reaction between the metallic magnesium and the alkyl or phenyl halide can be carried out at a temperature between about 20° C. and about 200° C., preferably between about 60° C. and about 100° C. This reaction must be carried out in the absence of oxygen. Thus, the reaction can be carried out under an atmosphere of an inert gas such as nitrogen or argon. The pressure is not critical and may vary between wide limits, but should be at least high enough to ensure that the reaction medium and the alkyl or aryl halide are substantially in a liquid state. It has also been found desirable to vigorously stir the reaction mixture.

The oxygen containing metal compounds of this invention have the general formula $(RO)_aM$ in which R, M and a are as defined.

Examples of the alkyl groups of the above formula include methyl, ethyl, n-propyl, isopropyl, n-butyl, isobutyl, sec.-butyl, t-butyl, the pentyls, the hexyls, the heptyls, the octyls and up to hexacosyls. Examples of aryl groups of the above formula include phenyl.

Illustrative of the oxygen containing metal compounds are the following: magnesium methoxide, magnesium ethoxide, magnesium propoxide, magnesium isopropoxide, magnesium butoxide, magnesium tert.-butoxide, aluminum methoxide, aluminum ethoxide, aluminum propoxide, aluminum isopropoxide, aluminum butoxide, aluminum tert.-butoxide, magnesium dibenzoate and aluminum tribenzoate.

The amount of oxygen containing metal compound that is added to the reaction product of the magnesium and the alkyl or phenyl halide is between about 0.05 and 2.0 mole per mole of organo-magnesium compound to be solubilized.

Preferably the amount is between about 0.10 and 1.0 mole per mole. More preferably the amount is between about 0.15 and 0.50 mole per mole.

The optimum quantity of the oxygen containing metal compound used depends upon the nature of the metal and "R" group of the oxygen containing metal compound, the particular alkyl or phenyl halide reactant and the particular hydrocarbon dispersion medium used, but can be easily determined by routine experimentation, well within the skill of those in the art.

The addition of the oxygen containing metal compound and subsequent steps must be carried out in the absence of oxygen. Thus, the addition and subsequent steps must be under an inert atmosphere of a gas such as nitrogen or argon.

In the practice of the process of the present invention, recoveries of about 40-70% of the theoretical amount of organo-magnesium can be achieved. The remaining portion of the original starting materials is presumably lost to thermal decomposition and coupling.

The solubilization of the organo-magnesium compound proceeds well at room temperature and is normally completed in two-three hours. However, to facilitate solubilization, the reaction mixture can be heated during the solubilization. The upper temperature limit for this step is dependent upon the decomposition temperature of the particular oxygen containing metal compound used, the decomposition temperature of the dialkyl magnesium compounds and the boiling point of hydrocarbon solvent in the absence of any applied pressure. During the addition of the oxygen containing metal compound, it is desirable to vigorously stir the reaction mixture.

The oxygen containing metal compound can be added to the reaction mixture of the magnesium and alkyl or phenyl halide either during or after the completion of the reaction or at both times.

Preferably it is added after the completion of the reaction as a solution in a hydrocarbon as previously defined with vigorous stirring.

The reactant mixture obtained after the addition of the oxygen containing metal compound is normally filtered and the solid washed with several portions of the hydrocarbon solvent used. The resultant wash solution can then be added to the filtrate.

After filtration of the reaction mixture, the resulting solution containing the organo-magnesium complexes of the present invention can then be diluted or concentrated as desired. The complexes can be isolated by evaporating the solvent to yield the viscous liquid or solid complex. However, it is preferred to handle these complexes in solution.

It is apparent to one skilled in the art that the complexes of the present invention are a mixture of complexes having different values for m and n and that the m/n value as used herein is an average value for these numbers. It is not necessary, or even desirable, to isolate individual complexes, however, since the mixtures work just as well as the individual complexes. Furthermore, it is recognized that a certain degree of group transfer occurs between the metal of the oxygen containing metal compound and the magnesium atoms of the complex. Thus, the formulae given for the complexes of the present invention are empirical rather than exact.

The complexes of the present invention are characterized by a high Mg/M ratio. They are further characterized by their freedom from undesirable contamination by halides. Furthermore, since the method of forming the complexes of the present invention does not require the use of an ether catalyst, the final product is completely ether-free.

Those compounds of the present invention which have sufficiently high Mg/M ratios (m/n of 4 or greater) can be useful in situations where organo-magnesium reagents are desired, i.e., the complexes can be used to simulate the "pure" organo-magnesium reagent in reactivity, since they can contain 80 mole percent or greater $R'_2Mg$. In this regard, the complexes of the present invention have the substantial advantage in that they are highly soluble in hydrocarbon solvents, whereas the pure organo-magnesium reagents are, in general, insoluble. Since these complexes are completely free of ether contamination, they can be used as Ziegler type catalysts without catalyst poisoning which may result from the ether contamination. Organo-magnesium compounds are effective catalysts for the polymerization of ethylene or propylene in the presence of titanium tetrachloride and, for the polymerization of 1,3-butadiene or 2-methyl-1,3-butadiene in the presence of titanium tetraiodide.

The present invention will be further illustrated by the following examples.

EXAMPLE I

To a 300 milliliter three neck flask equipped with a magnetic stirrer, reflux condenser, and addition funnel were added 7.7 grams (0.317 gram-atom) of magnesium powder (100 mesh) and 1.77 grams (0.019 mole) n-butyl chloride and a few crystals of iodine. All equipment was previously flushed while hot with dry nitrogen and all reactions and manipulations were carried out under a nitrogen blanket. The mixture was heated to 95° C. and the reaction initiated. Then 80 milliliters of heptane (previously dried over 4A molecular sieves) was charged to reaction mixture. Finally, 26.1 grams (0.282 mole) n-butyl chloride was charged by the addition funnel at a rate to maintain a gentle reflux after the addition of the heptane solvent. During the addition, the reaction mixture became very viscous and had a paste-like consistency. Heating was maintained at 95-97° C. for about one hour and then the mixture was allowed to cool to 30° C. Analysis showed the presence of no metal alkyl to be in the solution.

EXAMPLE II

To a reaction mixture of di-n-butylmagnesium at 85-90° C. prepared using 150 milliliters of heptane as described in Example I was added 11.0 grams (0.096 mole) of magnesium ethoxide. The mixture was stirred for one hour at 90-95° C., cooled and filtered. The filtrate contained 2.12 grams of magnesium or 0.087 mole of butylmagnesium ethoxide as a 23.5 weight percent solution. This represents a 29.1% yield of di-n-butylmagnesium based on butyl chloride.

EXAMPLE III a. To a reaction mixture of di-n-butylmagnesium at 80° C. prepared as described in Example I was added 19.5 grams (0.05 mole) of aluminum tribenzoate. The reaction temperature rose to 90° C. and was held there for two hours. The reaction was then allowed to cool, was filtered and washed.

The filtrate (90 grams) contained 1.35 grams magnesium or 0.0627 mole of di-n-butylmagnesium as a 9.65 weight percent solution. The filtrate also contained 0.324 gram aluminum or 0.012 mole of aluminum tribenzoate as a 5.20 weight percent solution, yielding a magnesium to aluminum ratio of 5.23. The yield of di-n-butylmagnesium based on butyl chloride was 42%.

b. Repeating the above procedure (IIIa) using 39 grams (0.1 mole) aluminum tribenzoate resulted in the recovery of 0.855 gram magnesium or 0.035 mole of di-n-butylmagnesium as a 5.39 weight percent solution. The filtrate also contained 0.207 gram of aluminum or 0.0077 mole of aluminum tribenzoate as a 3.34 weight percent solution yielding a magnesium to aluminum ratio of 4.607. The yield of di-n-butylmagnesium based on butyl chloride was 23%.

EXAMPLE IV a. A preparation of di-n-butylmagnesium was made as described in Example I except benzene rather than heptane was used as solvent. Excess magnesium powder (10.4 grams, 0.428 gram-atom) slurried in 371 grams of dry benzene was allowed to react with a total of 19.7 grams (0.213 mole) of n-butyl chloride. After addition of n-butyl chloride, 2.4 grams (0.012 mole) of solid aluminum tri-isopropoxide was added and the slurry was refluxed for two hours. After cooling to ambient temperature, the slurry was filtered. Analysis of the filtrate gave a recovered yield of 45.4% for soluble di-n-butylmagnesium based on n-butyl chloride and a Mg/Al ratio of 6.5.

b. Another preparation of di-n-butylmagnesium was made in benzene solvent, but a higher ratio of aluminum tri-isopropoxide was added. Analysis of the filtrate indicated a di-n-butylmagnesium yield of 48.9% and a Mg/Al ratio of 5.

We claim:

1. A hydrocarbon soluble organo-magnesium complex of the formula

wherein R is the group

wherein $R^2$ is a hydrocarbyl group, M is a group IIA or IIIA metal, and a is the integer 2 when M is a group IIA metal and 3 when M is a group IIIA metal; R' is a primary alkyl group having 1 to 25 carbon atoms, or phenyl group, or mixture thereof, and m and n are numbers such that the ratio of m/n is about one or greater.

2. A hydrocarbon soluble organo-magnesium complex solution comprising:
   (a) hydrocarbon solvent and dissolved therein
   (b) a complex having the formula

wherein R is the group

wherein $R^2$ is a hydrocarbyl group, M is a group IIA or IIIA metal, and a is the integer 2 when M is a group IIA metal and 3 when M is a group IIIA metal; R' is a primary alkyl group having 1 to 25 carbon atoms, or phenyl group, or mixture thereof, and m and n are numbers such that the ratio of m/n is about one or greater.

3. A hydrocarbon soluble organo-magnesium complex of the formula

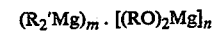

wherein R is a hydrocarbyl group, R' is a primary alkyl group having 1 to 25 carbon atoms, or phenyl group, or mixture thereof, and m and n are numbers such that the ratio of m/n is about one or greater.

4. The complex of claim 3 wherein R is a primary, secondary or tertiary alkyl group having 1 to 25 carbon atoms, R' is an alkyl group having 1 to 10 carbon atoms or phenyl and the ratio of m/n is between about 1 to 10.

5. The complex of claim 4 wherein R is a primary, secondary or tertiary alkyl group having 1 to 8 carbon atoms and R' is a primary alkyl group having 1 to 4 carbon atoms or phenyl.

6. The complex of claim 5 wherein R is a primary, secondary or tertiary alkyl group having 2 to 4 carbon atoms and R' is a primary alkyl group having 1 to 4 carbon atoms.

7. The complex of claim 6 wherein R is ethyl.

8. The complex of claim 7 wherein R' is n-butyl.

9. A hydrocarbon soluble organo-magnesium complex solution comprising:
(a) hydrocarbon solvent and dissolved therein
(b) a complex having the formula $(R_2'Mg)_m \cdot [(RO)_2Mg]_n$ wherein R is a hydrocarbyl group, R' is a primary alkyl group having 1 to 25 carbon atoms, or phenyl group, or mixture thereof, and m and n are numbers such that the ratio of m/n is about one or greater.

10. The solution of claim 9 wherein R is a primary, secondary or tertiary alkyl group having 1 to 25 carbon atoms, R' is an alkyl group having 1 to 10 carbon atoms or phenyl and the ratio of m/n is between about 1 to 10.

11. The solution of claim 9 wherein R is a primary, secondary or tertiary alkyl group having 1 to 8 carbon atoms and R' is a primary alkyl group having 1 to 4 carbon atoms or phenyl.

12. The complex of claim 1 wherein R is the group

wherein $R^2$ is an alkyl group having 1 to 20 carbon atoms or phenyl; M is magnesium or aluminum and a is the integer 2 when M is magnesium and 3 when M is aluminum; R' is an alkyl group having 1 to 10 carbon atoms or phenyl and the ratio of m/n is between about 1 to 10.

13. The complex of claim 12 wherein R is

wherein $R^2$ is an alkyl group having 2 to 4 carbon atoms or phenyl and R' is a primary alkyl group having 1 to 4 carbon atoms or phenyl.

14. The complex of claim 13 wherein R is

wherein $R^2$ is phenyl and R' is a primary alkyl group having 1 to 4 carbon atoms.

15. The complex of claim 14 wherein R is

wherein $R^2$ is phenyl and M is aluminum.

16. The complex of claim 15 wherein R' is n-butyl.

17. The solution of claim 2 wherein R is the group

wherein $R^2$ is an alkyl group having 1 to 20 carbon atoms or phenyl; M is magnesium or aluminum and a is the integer 2 when M is magnesium and 3 when M is aluminum; R' is an alkyl group having 1 to 10 carbon atoms or phenyl and the ratio of m/n is between about 1 to 10.

18. The solution of claim 2 wherein R is

wherein $R^2$ is an alkyl group having 2 to 4 carbon atoms or phenyl and R' is a primary alkyl group having 1 to 4 carbon atoms or phenyl.

19. A process for the preparation of hydrocarbon soluble organo-magnesium complex of the formula $(R_2'Mg)_m \cdot [(RO)_aM]_n$ wherein R is the group

wherein $R^2$ is a hydrocarbyl group, M is a group IIA or IIIA metal, and a is the interger 2 when M is a group IIA metal and 3 when M is a group IIIA metal; R' is a primary alkyl group having 1 to 25 carbon atoms, or phenyl group, or mixture thereof, and m and n are numbers such that the ratio of m/n is about one or greater comprising:
(a) reacting magnesium metal with primary alkyl halide or phenyl halide of the formula R'X wherein R' is as defined and X is chlorine, bromine or iodine at a temperature between about 20° C. and about 200° C. in the absence of oxygen, said magnesium being present in an amount from 1 to 2 moles of magnesium per mole of halide; and
(b) adding thereto in the absence of oxygen an oxygen containing metal compound of the formula $(RO)_aM$ wherein R, a and M are as defined in an amount equal to or less than a 1:1 mole ratio with the magnesium reaction compounds of step (a).

20. A process for the preparation of hydrocarbon soluble organo-magnesium complex of the formula $(R_2'Mg)_m \cdot [(RO)_2Mg]_n$ wherein R is a hydrocarbyl group, R' is a primary alkyl group having 1 to 25 carbon atoms, or phenyl group, or mixture thereof, and m and n are numbers such that the ratio of m/n is about one or greater comprising:
(a) reacting magnesium metal with primary alkyl halide or phenyl halide of the formula R'X wherein R' is as defined and X is chlorine, bromine or iodine at a temperature between about 20° C. and about 200° C. in the absence of oxygen, said magnesium being present in an amount from 1 to 2 moles of magnesium per mole of halide; and
(b) adding thereto in the absence of oxygen an oxygen containing metal compound of the formula $(RO)_2Mg$ wherein R is as defined in an amount equal to or less than a 1:1 mole ratio with the magnesium reaction compounds of step (a).

21. The process of claim 20 wherein step (a) is conducted in the presence of a hydrocarbon solvent.

22. The process of claim 20 wherein step (a) is conducted at a temperature between about 60° C. and about 100° C.

23. The process of claim 21 wherein said hydrocarbon solvent is an alkyl, cycloalkyl, aryl or alkaryl hydrocarbon having 6 to 15 carbon atoms.

24. The process of claim 19 wherein step (a) is conducted in the presence of a hydrocarbon solvent.

25. The process of claim 19 wherein step (a) is conducted at a temperature between about 60° C. to about 100° C.

26. The process of claim 24 wherein said hydrocarbon solvent is an alkyl, cycloalkyl, aryl or alkaryl hydrocarbon having 6 to 15 carbon atoms.

* * * * *